United States Patent
Carnevale

(10) Patent No.: US 9,016,862 B2
(45) Date of Patent: Apr. 28, 2015

(54) MULTIMODALITY CORRELATION OF OPTICAL COHERENCE TOMOGRAPHY USING SECONDARY REFERENCE IMAGES

(71) Applicant: Sonomed IP Holdings, Inc., Wilmington, DE (US)

(72) Inventor: Matthew Carnevale, Medford, MA (US)

(73) Assignee: Sonomed IP Holdings, Inc., Wilmington, DE (US)

( * ) Notice: Subject to any disclaimer, the term of this patent is extended or adjusted under 35 U.S.C. 154(b) by 237 days.

(21) Appl. No.: 13/815,432

(22) Filed: Mar. 1, 2013

(65) Prior Publication Data

US 2013/0301001 A1 Nov. 14, 2013

Related U.S. Application Data

(60) Provisional application No. 61/688,231, filed on May 10, 2012.

(51) Int. Cl.
*A61B 3/14* (2006.01)
*A61B 3/00* (2006.01)
*G06T 11/60* (2006.01)
*A61B 3/10* (2006.01)
*G06Q 40/00* (2012.01)

(52) U.S. Cl.
CPC ............ *G06T 11/60* (2013.01); *A61B 3/102* (2013.01); *G06Q 40/00* (2013.01)

(58) Field of Classification Search
USPC .................................................. 351/206, 246
See application file for complete search history.

(56) References Cited

U.S. PATENT DOCUMENTS

| | | | | |
|---|---|---|---|---|
| 7,997,728 | B2 * | 8/2011 | Huang et al. | 351/200 |
| 8,534,835 | B2 * | 9/2013 | Murata et al. | 351/206 |
| 2012/0140174 | A1 * | 6/2012 | Hee et al. | 351/206 |
| 2013/0169934 | A1 * | 7/2013 | Verdooner | 351/246 |

* cited by examiner

*Primary Examiner* — Jack Dinh
(74) *Attorney, Agent, or Firm* — Hayes Soloway PC

(57) ABSTRACT

Reference images from one or more OCT scanners are correlated with associated OCT scan data, which is in turn registered and correlated to a wide field image so as to present the OCT scan data registered and aligned to the correct location on the wide field image so as to permit displaying OCT scan data taken at different times or on different machines on a single screen all registered to the wide field image.

22 Claims, 5 Drawing Sheets

MULTIMODALITY CORRELATION OF OPTICAL COHERENCE TOMOGRAPHY USING SECONDARY REFERENCE IMAGES

FIELD OF THE INVENTION

This invention relates to optical coherence tomography (OCT) and more particularly to displaying the tomography scans from a number of tomographic sources.

BACKGROUND OF THE INVENTION

Typically one has OCT scans being done in a localized region of the eye with the result of the localized scan being displayed. In addition to this data from a localized area there are also other modalities that image a larger area of the eye or that image the eye in a different way, for example monochrome and color photography or laser scanning. It would be useful for the clinician to be able to look at those other modality images, and be able to see the OCT scans captured from another machine in alignment with the images.

The purpose is to allow the clinician can look at multiple exams of the patient's eye integrated into one screen. One of course one could display the images from different machines on different screens, but it is more helpful to the clinician to actually see the scans from the OCT and know which region of the eye they correspond to, as well as being able to see those features captured in a different way.

Thus in order to obtain the maximum amount of diagnostic information from all of these tests, there is a need for superimposing the images and the data associated with them. In short there is a requirement to compile them on top of one another and superimpose them together.

It is noted that the OCT scan provides valuable three dimensional cross sectional images of the eye which means one can see into tissue that is not visible just by observation. Thus, typically what happens is that during an OCT exam one can image a small area very densely but it takes quite a bit of time. Thus, there are limits on how much data one can process in one exam.

So typically what happens for instance if someone wants to image the macula one images a small region around just the macula. If someone has a problem with an optic nerve one images just a small region around the optic nerve. The trouble is that one is currently unable to look at all of the different areas together at one time. One can either look at the exam on the optic nerve or look at the exam on the macula. As a result there is a need for the ability to look at one large image of the eye and then to see all the different scan locations together on one screen.

In the past there have been a couple of attempts with correlating images and this is usually done by generating what is called an enface image. In taking an enface image one takes the depth scans of the dense OCT data and generates the enface image or a summation image. This means one uses the B scans and provides a calculated summation to create an image, namely a forward facing image from that data which looks like a photograph or an image one would see looking at the eye, but the resolution is very low and of very low quality. A lot of times it can have motion induced artifacts as the patient moves his eyes during the examination with the result that one does not obtain good resolution. So for instance in the middle of the scan the patient may be looking forward and then halfway through the scan their eye makes a quick movement to the side or up and down. As a result, The OCT can have a gap in it and the data can be misaligned so when one creates that enface image it's not real. It has errors in it and it presents an issue when one tries to register that feature or data against the other image of the eye to try to find the location where it fits.

In order to solve this problem in the past clinicians would create these summation images and they would try to register them manually against another image of the eye. However, when one has such errors, it makes it very difficult to align the blood vessel patterns. If the blood vessel patterns do not match, automatic alignment will fail.

Also just being an enface image, the resolution of the OCT scan is always lower than the actual resolution of the reference image so it is difficult to get a good alignment, especially if there are no very clear structures that are visible to the eye.

SUMMARY OF THE INVENTION

In order to solve this problem, one uses the reference image generated by the OCT scanner, and not by creating an enface image and registering to it. In the subject invention one accesses the reference images that all OCT scanners have available and use to display local OCT features, data or images. Note these reference images are usually imaged by a video camera, digital camera or a scanning laser ophthalmoscope or similar instrument that is creating a much better, higher quality image of the eye at the time of or slightly before or slightly after the scan.

The next step is to take this reference image, and compare it against the wider field image of the eye that you wish to register the OCT data to. One does this by finding a region in the wider image where one can fit the reference image inside and perform a registration to find a perfect match feature for feature. Then one knows the location of where the OCT scan was done on the wide field image of the eye.

After one ascertains the exact location of the particular features that one is trying to look at what is presented is as follows.

It will be appreciated that there are a few different things one can present. One can present a series of scan lines that actually show the physician where the OCT scans are in the wide field image and a clinician can click on the scan lines or scroll through them and see the corresponding B scan. Another thing one can do is to take data that is calculated from the OCT scan data and display the calculated data in an image on top of the scan area. For instance, from each OCT scan a thickness is derived so that in one embodiment an automated algorithm goes through each B scan from the top layer to the bottom layer, with the difference between the two displayed as the retinal thickness. Additionally one can create a color chart in the form of a topography map of the thickness of the retina and display the topology chart at the appropriate location on the wider field image of the eye.

In the past these composites are not correlated to any other image except for that reference image. So in the subject invention what is shown is the relevant OCT data or images directly on the wider field image representations of the eyes which is where that scan data belongs.

The net result is that one can compare OCT images of the eye taken from different machines or at different times due to the registration with the ubiquitous reference images produced by all OCT machines. One can view improvement or deterioration of the patient's eye by the correlation and registration process. One can even compare results of the same eye using OCT scans taken from different types of OCT machines. For example, if a patient was imaged with an OCT scanner from one manufacturer, and then years later they were imaged with an OCT scanner from another manufacturer, the two scans could be correlated together allowing the physician to interpret change in pathology using this invention.

In summary, there have been a few attempts by others to register OCT exam data to other imaging modalities.

These attempts have been accomplished by creating an enface image (or summation image) using the OCT volume scan data. This results in a low-resolution pseudo 2 dimensional image of the eye.

The prior attempts use this enface image to correlate and register against other imaging modalities has been problematical at best, most especially because the registration can only be done using an OCT volume cube scan, and not with high-resolution raster scans. As noted above, the resolution of the enface image is very poor and makes automated registration challenging which fails quite often because there is movement of the eye during the OCT scan, which corrupts the features of the enface image and causes the registration to fail.

In contradistinction the subject invention does not generate an enface image for registration.

Since many modern OCTs today have secondary reference imagers integrated into their design, which provide a real-time, high resolution view of the eye during the OCT scan (such as a digital fundus camera, SLO, LSLO or video camera) these references images are used in the registration process.

These OCT systems save a snap-shot frame of the eye from this reference imager, and store information indicating where the scan was performed relative to the reference image. While these images are not made readily available to the user, they can be extracted from the system if one knows their location and how they are stored in the OCT's computer.

These reference images are of much higher quality than an enface image, and do not suffer from any motion that occurred during the scan, which will result in a much higher probability of a successful match under challenging conditions, which would otherwise be impossible to achieve.

If the OCT employs an active tracking mechanism while scanning, the OCT can have very accurate registration of OCT data in relation to its secondary reference image.

As a result, this invention performs automatic registration of this secondary reference image against images from other modalities, and uses the results of the registration to align the OCT scans to the outputs of other imaging machines or modalities.

BRIEF DESCRIPTION OF THE DRAWINGS

These and other features of the subjection invention will be better understood in connection with the Detail Description in conjunction with the Drawings, of which.

DETAILED DESCRIPTION

Figure 3:
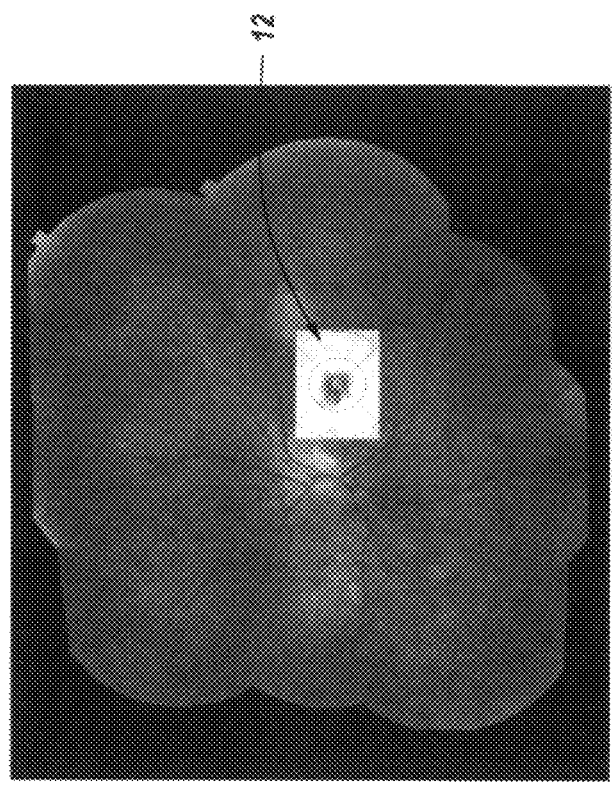
FIG. 3 is a photograph of the wide field image of FIG. 1 with OCT scan data registered and aligned to the correct location on the wide field image.
Figure 1:
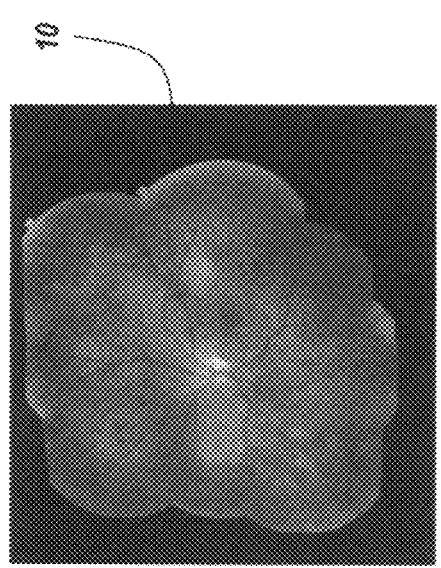
FIG. 1 is a photograph of a wide field photographic mosaic image of the retina of a patient on whom an OCT scan is performed.
Figure 2:
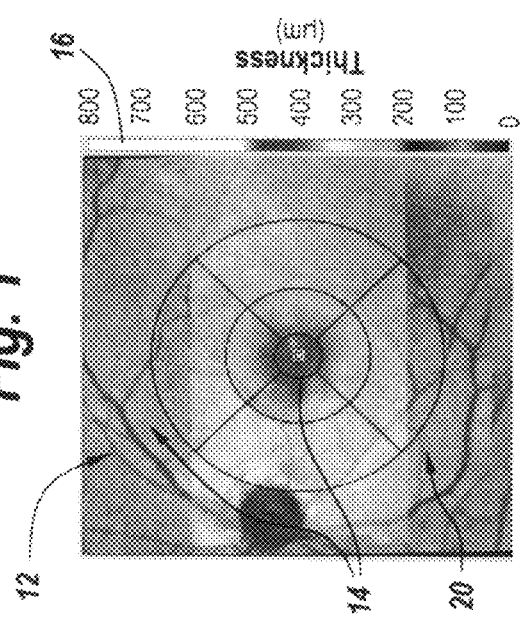
FIG. 2 is a photograph of OCT scan data and a reference image for the patient of FIG. 1.

Referring now to FIG. 1, the purpose of this Figure along with FIGS. 2 and 3 is to show how the subject system registers OCT scan data to a wide field photography mosaic of the eye of the patient undergoing an OCT scan. It will be noted that there are a number of ways to generate a mosaic of the eye such as that shown in FIG. 1 by reference character 10. In one example this is done by a series of photographs of smaller regions of the eye and by controlling the patient's gaze one can image different areas. Thereafter these areas are all automatically stitched together by an algorithm to create a wide field image. There are also some devices such as manufactured by Optos which create an Optomap to generate an image like the one shown in FIG. 1 with one shot that creates the wide field image. It should also be noted that although the drawings depict images of the retina, the same methods can also be applied to OCT scans and images of the anterior segment of the eye.

Referring now to FIG. 2, what is shown is an example of a reference image 12 from an OCT scanning process in which one wants to analyze the B scans to extract thickness values and create a topography map. This topography is shown by the shaded regions 14, with the shading being dictated by the gradient bar 16 to the right which describes thickness of the scanned region. Area 20 represents about 19 or 20 B scans over the region from which the thickness is extracted. Thereafter the topological map is created to show by different densities the corresponding thickness is. Thus, one is overlaying the OCT reference image with a topological thickness map.

Referring now to FIG. 3, what is shown is the result of the registration and alignment afforded by the subject invention, the result of which is to take the reference image 12 from FIG. 2, correlate and register it to the wide field image 10 of FIG. 1 and then display the topography map data on the mosaic in the same location at which it was acquired. The result is that the OCT scan data is registered to the wide field photographic mosaic.

Figure 4:
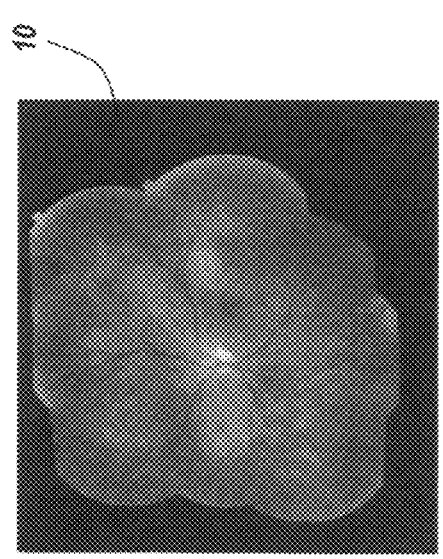
FIG. 4 is a photograph of a wide field photographic mosaic image of the retina of a patient on whom an OCT scan is performed in which OCT B Scan lines are to be registered and presented.
Figure 5:
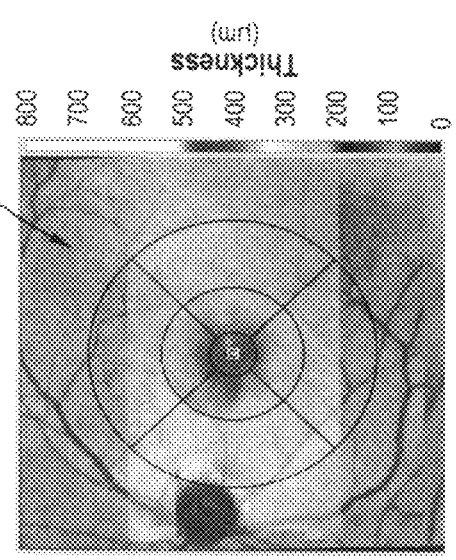
FIG. 5 is a photograph of the OCT scan data and reference image carrying B Scan data for the patient of FIG. 4.

Referring now to FIG. 4, again the wide field photography mosaic image 10 is presented, along with the OCT scan data and reference image 12 in FIG. 5.

Figure 6:
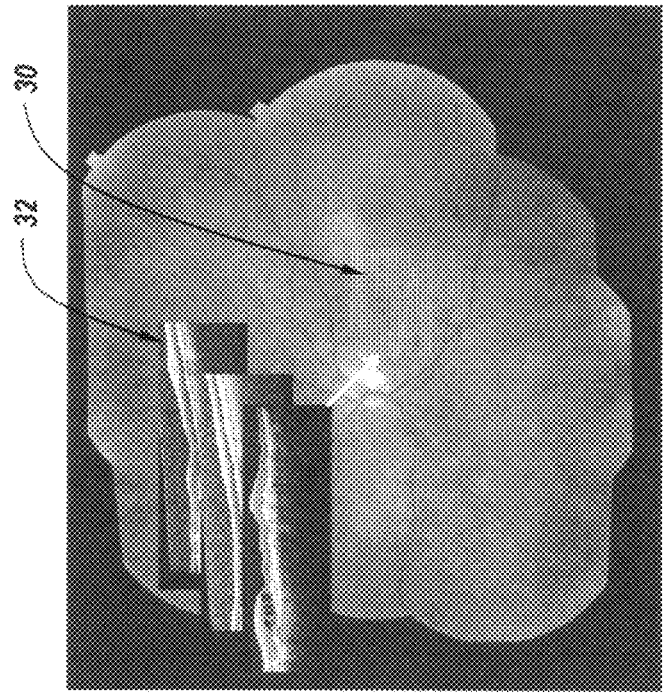
FIG. 6 is a photograph of the wide field image of FIG. 4, showing B Scan lines registered to the mosaic of FIG. 4 and displaying a magnified view of the B Scan lines adjacent the area of the eye that is scanned.

Referring now to FIG. 6, what is shown is another way to display this data. Instead of displaying the thickness of the topography map, one can actually display scan lines 30 that correspond to each individual B scan that was taken. Thus, if one wants to see a cross-section for that exact region of the eye one can click on the line and redisplay the cross-sectional image from the OCT B scan as illustrated 32. It is noted that the scan lines represent all of the OCT B scans that were used to create the aforementioned thickness map.

As a result, instead of using the thickness map one can click on an area of interest and obtain the B scans right around the clicked region.

Figure 7:
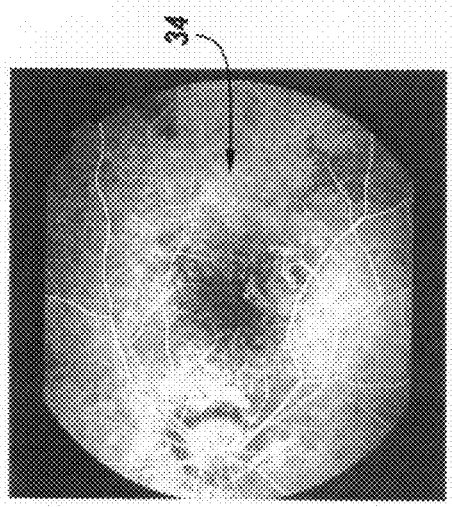
FIG. 7 is a fluorescein angiogram photograph of the eye of a patent providing a wide field of view of the patient's retina.

Referring to FIG. 7, what is shown is a fluorescein angiogram photograph 34. This is an image of the retina where a fluorescein dye is injected and the photographs are captured in a time sequence with a series of filters so that one can isolate a narrow bandwidth of the spectrum to actually see the dye and how the dye fluoresces as it goes through the veins, with the dye basically illuminating certain vascularization.

Referring now to FIG. 8, is again what is shown is the same OCT reference image 12 with the topography map superimposed on top.

Figure 9:
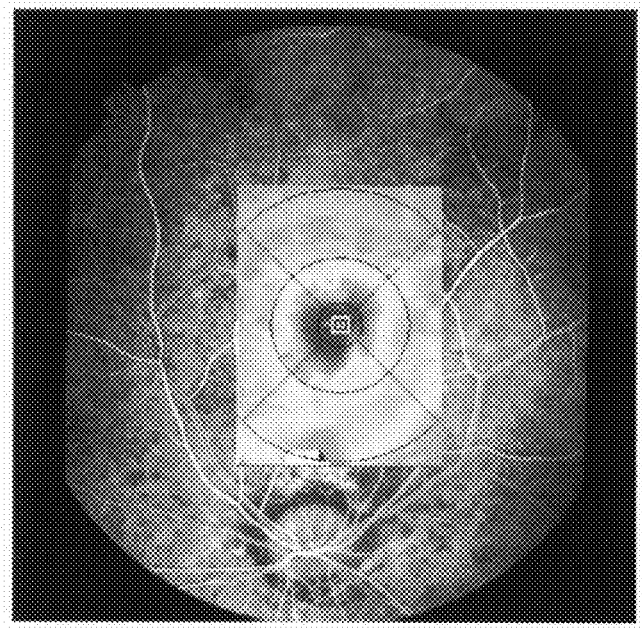
FIG. 9 is a photograph of the fluoresein angiogram photograph of FIG. 7 with OCT scan data registered and aligned to the correct location on the fluorescein photograph of FIG. 7.
Figure 8:
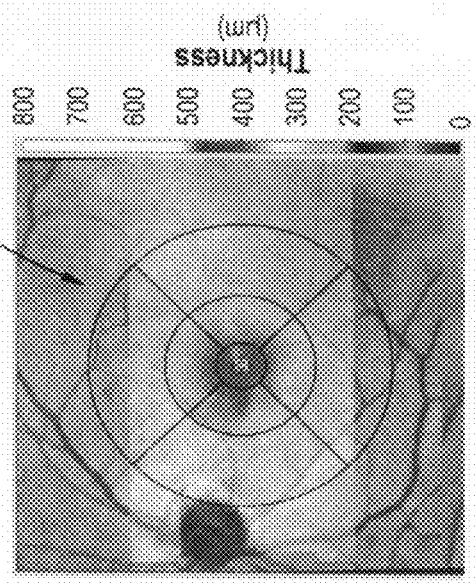
FIG. 8 is a photograph of OCT scan data and reference image associated with the fluorescein angiogram of FIG. 7.

Referring to FIG. 9, the result of the correlation or registration of the reference image to the fluorescein angiogram is shown in which the OCT scan and reference image of FIG. 8 is overlain onto angiogram 34, with the placement of the corresponding thickness map from FIG. 8 on top of the fluorescein angiogram in the correct location.

Figure 10:
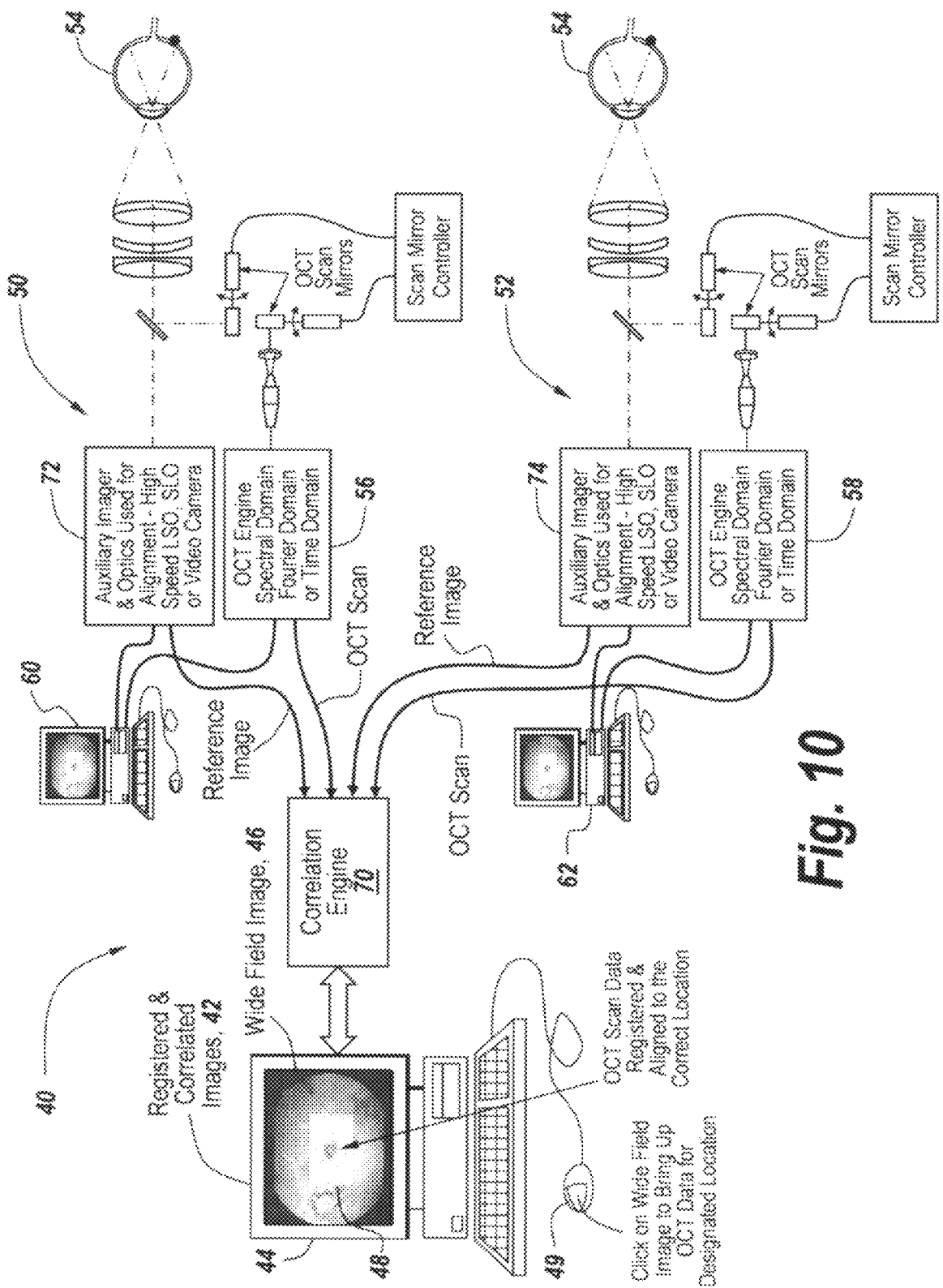
FIG. 10 is a diagrammatic illustration of the use of reference images from two different OCT scanners along with the OCT data therefrom to present OCT scan data registered and aligned to a wide field image of the eye for ease of interpretation; and, FIG. 11 is a flow chart of the operation of the subject system showing the image registration process followed by an output transformation matrix, in turn followed by the application of the matrix to OCT position data to correlate OCT position data to target image data.

Referring now to FIG. 10, the subject correlation, registration and alignment system 40 is used to take the outputs of one or more OCT scanners and present registered and correlated images 42 on a display 44 in which OCT scan data is registered and aligned to the correct location on a wide field image 46 such that this registered and aligned data 48 is viewable as overlaying the wide field image 46.

It is the purpose of the subject system to be able to click on the wide field image using a mouse 49 to be able to bring up the associated OCT data for the designated location.

It will be appreciated that the OCT data may be the result of the scan of one portion of the eye or another and that in the past there was no ready ability to analyze OCT data at various regions of the eye, all displayed against a wide field image. This is because in the past the OCT data was not registered and aligned with any wide field image. As a result, OCT scans on various sheets or screens had to be analyzed separately which was inconvenient at best.

The analysis of OCT scan information was made even more complicated when data from different OCT machines scanning the same eye was to be used in diagnosing a patient. The OCT scans could for instance be performed on the same machine on the same eye at different times or on different types of machines using different modalities.

As illustrated at 50 and 52 different OCT scanning machines are utilized to scan the same eye 54 of an individual with the output of the scan from OCT engines 56 and 58 respectively displayed at displays 60 and 62.

Thus, it was possible for a clinician to view the OCT scan results from two different OCT engines on two different displays, with the same eye having been scanned by the two engines.

While there could be a correlation between the OCT scans from engines 56 and 58, up until the present time there was never an attempt to display the OCT scan results on a single display having a single wide field image of eye 54.

The subject correlation, registration and alignment system accomplishes this type of display using a correlation engine 70 into which is fed the outputs of OCT engines 56 and 58, as well as a secondary reference image generated by an auxiliary reference imager 72 in the case of OCT engine 56 and auxiliary reference imager 74 in the case of OCT engine 58.

As mentioned before, it is very common for OCT scanners to generate secondary or auxiliary reference images for use in the respective systems. However, by accessing these internally-generated reference images and utilizing correlation engine 70 one can correlate, register and align the images from OCT scanners 50 and 52 to present to the clinician OCT data from the same eye, with the OCT data aligned with the correct location on the single wide field image, namely the location at which the scans were taken.

The result is that one can take OCT scans of an individual's eye either at various times using the same OCT scanner or can scan the individual's eye using different scanners and different modalities and yet present the scan results correlated to the original position of the eye.

This presents the clinician with the ability to click on one location in the wide field image and view superimposed scans from either different OCT scanners or from the same OCT scanner which scans the patient's eye at different times. In this manner the progression of eye disease can be tracked at the exact location on the wide field image that was scanned, or OCT data from scans at different positions in the wide field image can be presented simultaneously to give the clinician an overall view of the individual's eye health from various points of view.

Figure 11:
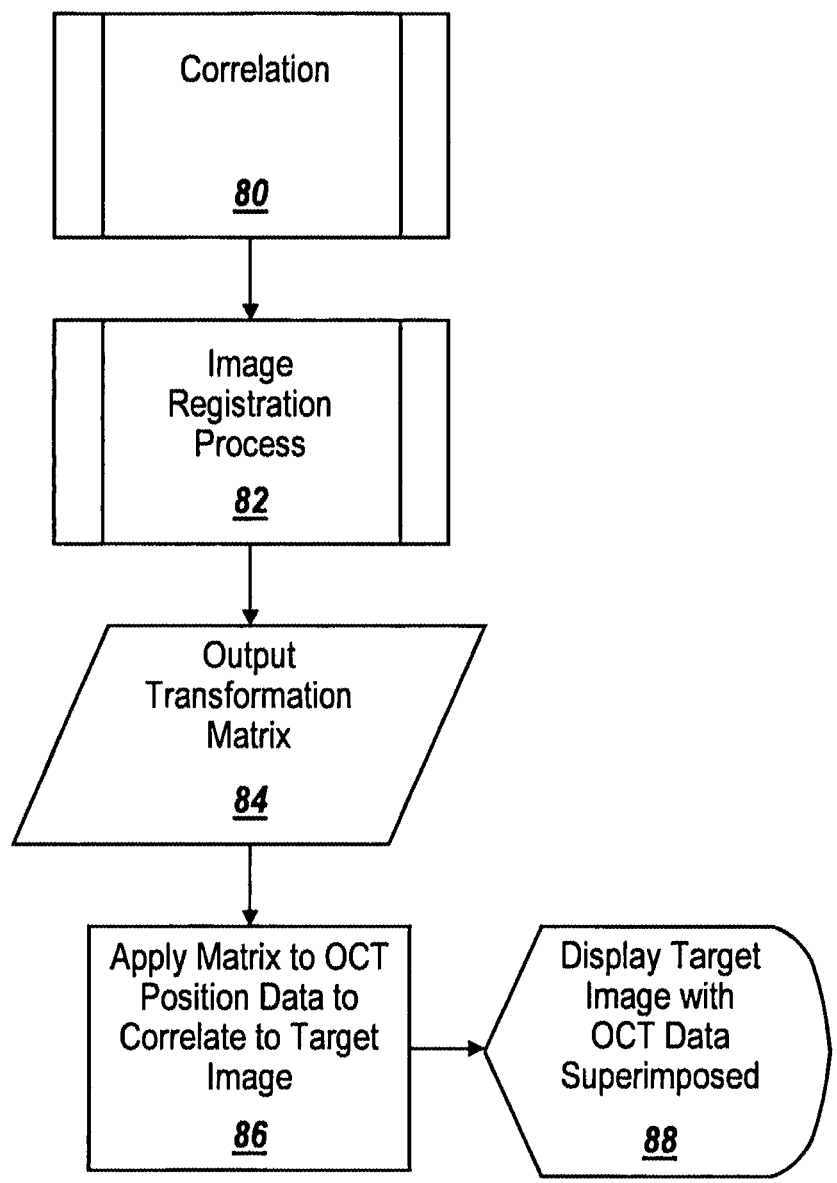

Referring now to FIG. 11, the correlation engine 70 performs a correlation process 80 which correlates blood vessel patterns and bifurcations in the references image to the same blood vessel patterns and bifurcations in the image from the other modality. The result of the correlation is passed through an image registration process 82 which computes a transformation matrix, mapping the coordinate system of the reference image to the coordinate system of the wide field image. The transformation matrix 84 is applied to an OCT position data step to correlate the data to the target image as illustrated at 86. Thereafter, the target image is displayed with OCT data superimposed as illustrated at 88. Note, in this case that the target image corresponds to the wide field image in FIGS. 1, 4, 7 and 10.

Note that one can use commercially available algorithms for aligning retinal images which after transformation are applied to pre-positioned OCT data. One such set of algorithms is the DualAlign Registration suite, called I2K Retina.

As will be appreciated, there are numerous advantages to the subject system, the most important of which are the composite view of the eye which is the ability to have multiple diagnostic information results in one view. Thus, instead of having to look at test after test, one has one screen that shows everything about the patient's eye.

The other major advantage is that there is a system to correlate diagnostic information between two unrelated modalities.

For example, a physician may see certain OCT data on the reference image and may see something different when the OCT scan data is correlated to a fluorescein angiogram that he wouldn't have noticed before. For example, in the fluorescein angiogram the physician may see a leak or a lesion or on a color photo they may see some discoloration or some elevation. The ability to see that data and then be able to see other OCT data displayed on the same region of the wide angle image at the same time can provide a significant improvement in diagnostic capability.

While the present invention has been described in connection with the preferred embodiments of the various figures, it is to be understood that other similar embodiments may be used or modifications or additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. A method for presenting OCT exam data registered in position with images from other imaging modalities, comprising the steps of:
    extracting secondary reference data from the secondary reference imager of an OCT machine;
    generating an OCT scan registered to the secondary image data; and,
    performing automatic registration of the secondary reference image against an image associated with the other modality, the registration results being used for aligning the OCT scan with the image associated with the other modality.

2. The method of claim 1, wherein the registration is accomplished utilizing the DualAlign i2k retina algorithm.

3. The method of claim 1, wherein the other imaging modality includes a wide field mosaic which was created by stitching together multiple images of the eye such that the OCT scans are aligned to the image provided by the wide field mosaic.

4. The method of claim 1, wherein the other imaging modality generates a single wide field image of the eye captured in a single acquisition such that the OCT scans are aligned to the image provided by the wide field image.

5. The method of claim 1, wherein the imaging modality includes an image of fluorescent emission created by an excitation light source and wherein the OCT exam data is aligned to the fluorescent emission image.

6. A method for presenting on a single screen the OCT scan data results of OCT scans taken of an eye at different times or on different machines comprising the steps of:
    obtaining from an OCT scanning machine secondary reference data and OCT scan data registered thereto;
    obtaining a wide field image of the eye associated with the scan data; and,
    registering and correlating the reference image with the associated OCT scan data to the location on the wide field image at which the scan data was taken.

7. The method of claim 6, wherein the wide field image includes a number of stitched together images of the eye.

8. The method of claim 6, wherein the wide field image includes an image of fluorescent emission created by an excitation light source.

9. The method of claim 6, wherein the wide field image includes a single wide field image of the eye captured in a single acquisition step.

10. The method of claim 6, wherein the scan data is presented on the reference image at the point on the reference image at which the scan took place.

11. The method of claim 10, and further including the step of converting the scan data to thicknesses of the eye layers at the scanned location.

12. The method of claim 11, wherein the thicknesses are displayed registered with the reference image such that the scan thickness data is presented correctly located on the wide field image.

13. The method of claim 6, wherein the OCT scans are performed at different times and wherein the OCT scan data from the scans performed at different times is registered to the reference image in an overlapping fashion, whereby changes in the eye can be seen due to the registration of the scan data taken at different times on the reference image.

14. The method of claim 6, wherein two OCT scanning machines are utilized to scan the eye and wherein the reference images and the OCT scan data from the two OCT scanning machines is correlated to present scan data from the two OCT scanning machines registered and correlated to the wide field image.

15. The method of claim 6, wherein the single screen is a computer screen and further including the step of selecting on the computer screen the point on the wide field image at which OCT scan data is to be presented, whereby a clinician can click on the computer screen and bring up the OCT scan data for the selected location on the wide field image.

16. The method of claim 13 wherein the OCT scan data is represented as a change in thickness of layers of the eye between the OCT scans taken at different times.

17. Apparatus for presenting OCT exam data registered in position with images from other imaging modalities, comprising:
    an OCT scanning machine adapted to scan an eye, said OCT scanning machine outputting OCT scan data and having a secondary reference imager, said OCT scanning machine generating a secondary reference image from said secondary reference imager;
    a wide field image of said eye generated from a wide field imaging modality;
    a correlation engine for generating OCT scan data registered to said secondary reference image data, said correlation engine performing automatic registration of the said secondary reference image and associated OCT scan data against said wide field image, the registration automatically aligning said OCT scan data with the location of the scan on said wide field image, and,
    a display for displaying the aligned scan data with said wide field image.

18. The Apparatus of claim 17, wherein said registration is accomplished utilizing the DualAlign i2k retina algorithm.

19. The Apparatus of claim 17, wherein said wide field imaging modality includes a wide field mosaic which was created by stitching together multiple images of the eye.

20. The Apparatus of claim 17, wherein said wide field imaging modality includes a wide field image of the eye captured in a single acquisition step.

21. The Apparatus of claim 17, wherein said OCT scan data includes OCT scans, wherein said wide field imaging modality includes a wide field mosaic which was created by stitching together multiple images of the eye and wherein said OCT scans are aligned to the image provided by said wide field mosaic.

22. The Apparatus of claim 17, wherein said OCT scans are converted to a rendition of thickness or change in thickness of layers of the scanned region of said eye.

* * * * *